US011802168B2

(12) United States Patent
Stengel

(10) Patent No.: US 11,802,168 B2
(45) Date of Patent: Oct. 31, 2023

(54) POLYDEXTROSE MATERIAL

(71) Applicant: CARGILL, INCORPORATED, Wayzata, MN (US)

(72) Inventor: Bruno Frederic Stengel, Auderghem (BE)

(73) Assignee: Cargill, Incorporated, Wayzata, MN (US)

(*) Notice: Subject to any disclaimer, the term of this patent is extended or adjusted under 35 U.S.C. 154(b) by 0 days.

(21) Appl. No.: 15/363,949

(22) Filed: Nov. 29, 2016

(65) Prior Publication Data

US 2017/0081427 A1    Mar. 23, 2017

Related U.S. Application Data

(63) Continuation of application No. 13/058,763, filed as application No. PCT/EP2009/005332 on Jul. 23, 2009.

(30) Foreign Application Priority Data

Aug. 20, 2008 (EP) .................................. 08014774

(51) Int. Cl.
| | |
|---|---|
| C08B 37/00 | (2006.01) |
| A23G 1/40 | (2006.01) |
| A23G 3/42 | (2006.01) |
| A23L 2/02 | (2006.01) |
| A23L 2/52 | (2006.01) |
| A23L 29/212 | (2016.01) |
| A23L 33/26 | (2016.01) |
| A61K 8/73 | (2006.01) |
| A61K 47/26 | (2006.01) |
| A61Q 19/00 | (2006.01) |

(52) U.S. Cl.
CPC ............ *C08B 37/0009* (2013.01); *A23G 1/40* (2013.01); *A23G 3/42* (2013.01); *A23L 2/02* (2013.01); *A23L 2/52* (2013.01); *A23L 29/212* (2016.08); *A23L 33/26* (2016.08); *A61K 8/73* (2013.01); *A61K 47/26* (2013.01); *A61Q 19/00* (2013.01); *A23V 2002/00* (2013.01)

(58) Field of Classification Search
CPC ................ C08B 37/0009; A61K 47/26; A23V 2250/51; A23V 2250/5116
USPC ......................................................... 426/658
See application file for complete search history.

(56) References Cited

U.S. PATENT DOCUMENTS

| | | | |
|---|---|---|---|
| 3,766,165 A | 10/1973 | Rennhard | |
| 3,876,794 A | 4/1975 | Rennhard | |
| 4,282,836 A | 8/1981 | Fox et al. | |
| 4,556,578 A | 12/1985 | Meyer | |
| 4,622,233 A | 11/1986 | Torres | |
| 4,828,836 A | 5/1989 | Elger | |
| 5,051,500 A | 9/1991 | Elmore | |
| 5,091,015 A | 2/1992 | Bunick et al. | |
| 5,262,187 A | 11/1993 | Hahn | |
| 5,620,873 A | 4/1997 | Ohkuma et al. | |
| 5,660,872 A † | 8/1997 | Van Loo | |
| 5,831,082 A † | 11/1998 | An | |
| 6,559,302 B1 | 5/2003 | Shah et al. | |
| 2004/0038837 A1 | 2/2004 | Pereira | |
| 2004/0213882 A1 | 10/2004 | Lauridsen | |
| 2005/0025721 A1 | 2/2005 | Holme et al. | |

FOREIGN PATENT DOCUMENTS

| | | |
|---|---|---|
| CN | 1056697 A | 9/2000 |
| CN | 1215730 C | 8/2005 |
| CN | 1320089 C | 6/2007 |
| CN | 101043822 B | 1/2011 |
| EP | 0458748 | 11/1991 |
| EP | 1629727 A1 | 3/2006 |
| JP | 2936337 B2 | 8/1999 |
| WO | 98/41545 | 9/1998 |
| WO | 2004018609 A1 | 3/2004 |
| WO | 2006022544 A1 | 3/2006 |
| WO | 2010/020321 | 2/2010 |

OTHER PUBLICATIONS

Mitsubishi SAC 2011, downloaded from the internet at http://www.diaion.com/en/products/ion_01_lineup.html.
PCT International Search Report PCT/EP2009/005332, dated May 10, 2009, 2 pages.
Burdock, G. A. et al., "A review of the studies of the safety of polydextrose in food", Food and Chemical Toxicology, (19990000), vol. 37, pp. 233-264, XP055416322.
Food Additives Dec. 31, 2004 Liu Xuejun et al., Jilin Science and Technology Press Co., Ltd p. 233.
Food Chemistry and Nutrition Sep. 30, 2007 Ma Li, Beijing: China Light Industry Press pp. 305-306.
Functional Food Additives Jan. 31, 2006 Pan Daodong, Beijing: China Light Industry Press pp. 214-216.
Functional Food and Health Care Aug. 31, 2006 Deng Shunyang, Beijing: Science and Technical Documentation Press pp. 132-135.
Grenby, T. H. et al., "Properties of maltodextrins and glucose syrups in experiments in vitro and in the diets of laboratory animals, relating to dental health", British Journal of Nutrition, (20000000), vol. 84, pp. 565-574, XP055416320.
Lyn O'Brien-Nabors, Alternative Sweeteners, Third Edition, Revised and Expanded, (Jun. 8, 2001), ISBN 9780824704377.

(Continued)

*Primary Examiner* — Jeffrey P Mornhinweg

(57) ABSTRACT

The present invention discloses a new type of water-soluble polydextrose. This new type of polydextrose contains at least 75% by weight of saccharide molecules having a degree of polymerisation (DP) of 5 or more and characterised in that the non-digestible fiber content is at least 80% by weight. Further, the present invention relates to a process for preparing this new type of polydextrose and to the use of this polydextrose in products such as food products, pharmaceutical products and personal care products.

14 Claims, No Drawings

(56) References Cited

OTHER PUBLICATIONS

Nihon University Journal of Oral Science, vol. 15, No. 1 Dec. 31, 1989 Eiji Setsu Cariogenicity of polydextrose and refined polydextrose as a substrate pp. 1-11.
Practical Encyclopedia of Household Cosmetics Sep. 30, 2000 Zhang Yuchuan Beijing: Chemical Industry Press p. 190.
Practical Manual of Light Industrial Additives: Paper, Food, Printing and Dyeing Industry vol. Jul. 31, 2002 Li Yousen Beijing: Chemical Industry Press pp. 403-404.
S A S Craig, et al., "Chapter 18. Polydextrose as Soluble Fiber and Complex Carbohydrate", S A S Craig, et al., Leon Prosky, Susan Sungsoo Cho and Mark Dreher, Complex Carbohydrates in Foods, Marcel Dekker, XP055416309.
Setsu, E., "Polydextrose", Nichidai Koko Kagaku, (19890000), vol. 15, pp. 1-11, XP055416324.
Starch Derivatives 20010430 You Xin Beijing: China Materials Publishing House pp. 107-110.
Steve W. Cui, Food Carbohydrates: Chemistry, Physical Properties, and Applications, CRC Press, (May 23, 2005), ISBN 0-8493-1574-3.
Food Research and Development, vol. 21, No. 5 Oct. 31, 2000 Wan Yin et al., The production, properties and functions of polydextrose in foods pp. 30-34.

† cited by third party

POLYDEXTROSE MATERIAL

This application is a continuation of U.S. application Ser. No. 13/058,763, filed on Feb. 11, 2011, which is a National Stage Entry of International Application No. PCT/EP2009/005332, which was filed on Jul. 23, 2009, which in turn claims priority to European Patent Application No. 08014774.7, which was filed on Aug. 20, 2008, wherein the entireties of said patent applications are incorporated herein by reference.

TECHNICAL FIELD

The present invention relates to a new type of water-soluble polydextrose. This new type of polydextrose contains an increased amount of saccharide molecules having a higher degree of polymerisation (DP) and has a high non-digestible fiber content. Further, the present invention relates to a process for preparing this new type of polydextrose and to the use of this new polydextrose in products such as food products, pharmaceutical products and personal care products as well as to such products containing this polydextrose.

BACKGROUND OF THE INVENTION

Acid-catalysed polymerisation of saccharides is a well-known phenomenon which is described in numerous general articles, books and patents.

Polydextrose is commercially available and all of these polydextrose products include a variety of residual compounds such as glucose, sorbitol, citric acid and other compounds which contribute to the taste, colour, and caloric value. Low molecular weight compounds such as 1,6-anhydroglucose and 5-hydroxymethylfurfural contribute a bitter taste and off-flavour.

U.S. Pat. No. 3,766,165 discloses that polymers useful as low-calorie food ingredients can be prepared by heating dextrose or maltose, optionally with a minor amount of a polyol, in the presence of edible polycarboxylic acid catalysts under reduced pressure. U.S. Pat. No. 3,876,794 discloses various kinds of foods containing same.

In the wake of this important disclosure, further development and research is concentrated on overcoming the sour and/or bitter taste observed in the products according to U.S. Pat. Nos. 3,766,165 and 3,876,794.

E.g., WO 98/41545 discloses methods for preparing polysaccharides by reacting glucose or glucose containing materials with a polyol in the presence of mineral acids such as phosphoric, hydrochloric and/or sulphuric acid. According to this disclosure, the low levels of catalyst as suggested therein lead to minimal or no off-flavors and little color formed during the course of the reaction. The methods disclosed in this document may comprise further purification methods.

U.S. Pat. No. 5,831,082 describes a process for obtaining highly pure water-soluble polydextrose by separation. The reported over 99.2% water-soluble polydextrose contains considerable amounts of di-, tri- and tetrasaccharides. The products according to this disclosure are reported to not have a bitter aftertaste.

U.S. Pat. No. 5,051,500 describes a continuous method for preparing a randomly-bonded polysaccharide.

US 2004/0038837 relates to the use of maltodextrin (named here as well as polydextrose) in combination with sucrose to induce biphasic liquid formation. The mentioned product has a polymerisation degree of 4 to 22 and is brought on the market as Maltrine™, which corresponds to maltodextrin type products.

EP 0 458 748 describes a polydextrose composition that is substantially free of bitter tasting and colour. In example 1 the polydextrose solution is added to an anion exchanger. The eluate (containing polydextrose) is free from the citric acid, but lower molecular weight contaminants such as 1,6-anhydroglucose, sorbitol and glucose are still present.

U.S. Pat. No. 5,831,082 describes a process for obtaining a highly pure water-soluble polydextrose. The crude polydextrose which contains 0.5 to 3% of citric acid is purified by using a simulated moving bed system applying a strong acidic gel. The DP6+ fraction is always around 56-58% by weight.

In view of the prior art, there is still a considerable need for an improved water-soluble polydextrose material which contains an increased amount of saccharide molecules with a higher degree of polymerisation and a reduced number of digestible mono- and oligosaccharides. With the present invention, such a new kind of polydextrose is provided.

SUMMARY OF THE INVENTION

The current invention relates to a new water-soluble polydextrose containing at least 75% by weight of saccharide molecules having a degree of polymerisation of 5 or more. More preferably, the polydextrose contains at least 80% by weight of saccharide molecules having a degree of polymerisation of 5 or more, and characterised in that the non-digestible fiber content is at least 80% by weight, preferably at least 85% by weight, more preferably at least 90% by weight. In addition, the present invention provides a process for preparing such a polydextrose comprising the steps of a) providing crude polydextrose,
b) adjusting the pH to from 6 to 8 preferably about 7, and
c) chromatographic separation into at least two fractions, wherein one fraction is enriched in saccharide molecules having a degree of polymerisation from 1 to 4 and one fraction is enriched in said new water-soluble polydextrose according to the invention.

Moreover, the present invention relates to the use of this new polydextrose in the preparation of products such as food products, pharmaceutical products and personal care products, as well as to said food products, pharmaceutical products and personal care products containing this polydextrose.

DETAILED DESCRIPTION OF THE INVENTION

Polydextrose as referred to herein, is a water-soluble, bulking agent. It is a randomly cross-linked (branched) glucan polymer (polysaccharide) characterised by having predominantly β-1-6 and β-1-4 linkage and which is produced through acid-catalysed condensation of saccharides alone or in the presence of sugar alcohols. Polydextrose is substantially different from maltodextrin which is obtained through the hydrolysis of starch materials and which is containing a majority of α-1-4 linkages.

The new polydextrose according to the present invention is a polydextrose with an increased amount of saccharide molecules having a degree of polymerisation (DP) of 5 or more. The degree of polymerisation is applied as in polymer chemistry and refers to the number of repeat units in the chain. The degree of polymerisation is a measure of molecular weight and the molecular weight of the monomer is calculated as about 162. This increased amount of saccharide molecules with a DP of 5 or more is at least 75% by weight and more preferably, at least 80% by weight. The new polydextrose is further characterised in that the non-digestible fiber content is at least 80% by weight, preferably at least 85% by weight, more preferably at least 90% by weight. Non-digestible fiber is neither digested nor absorbed in the small intestine. It has at least one of the following properties: increase stools production, stimulate colonic fermentation, reduce fasting cholesterol levels, and/or reduced post-prandial blood sugar and/or insulin levels. The non-digestible fiber is determined by applying fresh dialysed rat small intestine powder at 37° C. at pH 6.

In a preferred embodiment, the polydextrose according to the invention further contains less than 20% of saccharide molecules having a DP from 1 to 4 (mono- and oligomers), and preferably the amount of these mono- and oligomers is less than 15% by weight, more preferably less than 10% by weight. With respect to the present invention, the terms "oligomer" and "oligosaccharide" are used to describe those products of a polymerisation reaction which have a DP from 1 to 4, i.e. they contain 1 to 4 moieties corresponding to a saccharide or sugar alcohol unit, e.g. 4 saccharide units or 3 saccharide and 1 sugar alcohol unit, each linked via covalent bonds such as glycosylic bonds. In contrast, those molecules resulting from the polymerisation reaction which have a degree of polymerisation of 5 or more are referred to as "polymers" or "polysaccharides". If, glucose or other hexose containing reactants are used in the polymerisation reaction, these polymers have a molecular weight of about 828 g/mol or higher.

Furthermore, the polydextrose according to the invention has a molecular weight dispersity below 2.0, or preferably, below 1.8, describing the dispersions of distributions of molar masses. The equivalent terminology is polydispersity. This is the ratio of weight average molecular weight to number average molecular weight.

The current invention further relates to a polydextrose according to the invention characterized by a volume mean diameter smaller than 60 µm, preferably smaller than 55 µm, and more preferably smaller than 50 µm. The calculation of the volume mean diameter is based on the definition of moments of a distribution and an example is given in ISO/FDIS 9276-2.

Finally, according to the present invention, the polydextrose is low caloric, and non-cariogenic. Its non-cariogenicity is measured with an in-vitro test.

Another embodiment of the invention is directed to a process for preparing the new polydextrose as defined above, which comprises the following steps:
 a) providing a crude polydextrose;
 b) adjusting the pH of the crude polydextrose of step a) to from 6 to 8, preferably about 7, e.g. by adding alkaline compounds; and
 c) chromatographic separation of the product of step b) into at least two fractions, wherein one fraction is enriched in saccharide molecules having a DP from 1 to 4, and one fraction which is enriched in polydextrose containing at least 75% of molecules, which have a DP of 5 or more.

In one embodiment, this process according to the invention provides the crude polydextrose in step a) by acid-catalysed polymerisation of saccharides.

The saccharides used in the first step of the process are preferably glucose and glucose-containing saccharides. These saccharides can be glucose (dextrose), maltose, starch hydrolysates, or the like, wherein a fraction of the saccharide moieties might also be esterified with carboxylic acids. These saccharides could be used in an anhydrous or in hydrated state, or they could be used in an aqueous solution.

Optionally, the saccharides used as starting material may further contain sugar alcohols. Preferably, the amount of sugar alcohols used in the starting material is from 0 to 20% by weight of polymerisation reactants (saccharides). These sugar alcohols can comprise one or more of glycerol, erythritol, threitol, pentitols such as xylitol, and hexitols such as sorbitol, mannitol or galactitol. Preferred sugar alcohols comprise one or more hexitols and, particularly, sorbitol.

A large range of acids could be used for catalysing the polymerisation to obtain the crude polydextrose in step a). Preferably, these catalysts are acids which are allowable for consumption in order to reduce the otherwise necessary controls and costs to check for the presence of and, if necessary, remove the catalyst acids from the final product. In particular, the preferred acids are edible acids (food grade acids) such as phosphoric acid, citric acid, malic acid, succinic acid, adipic acid, gluconic acid, tartaric acid, fumaric acid and mixtures thereof. Particularly preferred are citric acid and/or phosphoric acid. The amount of acid to be used as catalyst should be below 10 mol % relative to the amount of saccharide (and polyol, if present) starting material used in the polymerisation reaction. Preferably, this amount should be clearly below this level, such as e.g. at most 3, at most 1, at most 0.5, at most 0.1 mol % or lower.

The crude polydextrose is still containing the residual acid which is used in the polymerisation reaction.

In step b), the pH of the crude polydextrose is increased to 6 to 8, preferably about 7, by adding alkaline compounds. Surprisingly, it was found that by increasing the pH any formation of degradation products such as furans, furfural and 5-hydroxymethyl furfural (5HMF) was prevented during the subsequent separation step. The pH is increased preferably by adding liquid alkaline compounds, such as sodium hydroxide dissolved in water or other suitable alkalising compounds known in the art.

The chromatographic separation according to step c) leads to at least two fractions, wherein one fraction is enriched of mono- and oligosaccharide molecules, i.e. this fraction is enriched in dextrose, maltose and other oligomers (up to DP4) in comparison with the crude polydextrose after step b); and the other fraction is enriched in polysaccharides (preferably with polymerisation degree of 5 and higher) compared to the crude polydextrose after step b).

Preferably, the chromatographic separation is performed on a cation exchange resin, such as a strongly acidic cation (SAC) exchange resin.

Finally, the polydextrose of the current invention is free from degradation products such as furans, furfural and 5-hydroxymethyl furfural (5HMF) and through the chromatographic separation a new profile of polymerisation degree is obtained and the final product is low-caloric, non-cariogenic and has a non-digestible fiber content of at least 80%.

Another aspect of the invention is directed to the use of polydextrose containing at least 75% by weight of saccharide molecules having a DP of 5 or more and characterised in that the non-digestible fiber content is at least 80% by weight, in the preparation of products selected from the group consisting of food products, pharmaceutical products and personal care products. Still another aspect of the invention is directed to food products, pharmaceutical products and personal care products which contain such a new polydextrose. In these products, the polydextrose containing at least 75% by weight saccharide polymers and characterised in that the non-digestible fiber content is at least 80% by weight, can be used in addition or instead of conventional polydextroses.

The pharmaceutical products according to the invention comprise tablets, excipients for preparing tablets, viscosity agents for use in syrups or other liquid or viscous fluids, solutions, emulsions or suspensions.

The personal care products according to the invention are selected from fluid, semifluid or solid products such as tooth paste, mouth wash and the like.

The polydextrose according to the invention is useful as a humectant. Humectant is a substance used primarily in foods and cosmetic products to help retain moisture.

The polydextrose according to the invention is particularly useful for the preparation of food products. These food products comprise in particular confectionery, bakery products, beverages and diary products.

Confectionery compositions within the scope of the present invention include chocolate, crystalline and non-crystalline products. Non-crystalline products within the scope of the present invention include hard candies, brittle, caramel, toffee, licorice, jellies, chewing gums and gums, preferably soft gums. Crystalline products within the contemplation of the confectionery compositions of the present invention encompass fondants and creams, fudge, nougats, marshmallows, pralines, pressed candies such as tablets, marzipan and pastes, and panned candies (dragees). Combinations of these products are also within the scope of confectionery compositions. For example, chocolate coated crystalline or non-crystalline products.

Chocolate, an important confectionery composition within the contemplation of the present invention, encompasses sweet chocolate, semi-sweet chocolate, bitter-sweet chocolate, which as a group are often also referred to as dark chocolate, milk chocolate, buttermilk chocolate, skim milk chocolate and white chocolate. In addition, any of the aforementioned chocolates filled with nuts, fruits, rice and other fillings used in the chocolate arts are also within the scope of the current invention. Chocolate also includes any confectionery product having qualities sufficient to impart chocolate taste, chocolate flavour and any other material that performs as a chocolate analogue obtaining a tender cake. By applying the new polydextrose of the current invention, the chocolate, milk and/or dark chocolate, is low caloric. Furthermore in combination with erythritol, the final chocolate is non-cariogenic and the cooling effect of erythritol is reduced by the new polydextrose of the current invention.

The current invention further relates to bakery products comprising the polydextrose of the current invention and additional bakery ingredients.

The additional bakery ingredients will be apparent to a person skilled in the art. They may include, e.g.: flour, raising agents (such as baking powder and/or yeast), water and/or water-miscible liquids (such as milk, alcohols, etc.), sweeteners (e.g. sugar or artificial sweeteners), flavourings (e.g. synthetic or natural flavours such as vanilla, caramel and/or almond flavours; fruit juices such as orange, grapefruit, pear, cherry, raspberry and/or blackcurrant juices; vegetable extracts such as tomato, carrot, onion and/or garlic extracts; spices; herbs; etc.) and/or one or more natural or synthetic colorants. Optionally, vitamins (such as vitamins A, D3, E, K1, C, B1, B2, B5, B6, B12 and PP, folic acid and biotin) and minerals (such as sodium, potassium, calcium, phosphorus, magnesium, chloride, iron, zinc, copper, manganese, fluorine, chromium, molybdenum, selenium and iodine) can also be added.

The flour used in the bakery products may be from any source (e.g. corn flour, soy flour or wheat flour). Most preferably, however, it will be wheat flour. It is the protein of wheat flour, gluten, which distinguishes it from other flours and makes it of particular value in the baking industry. In hard, high-protein wheat, there is more gluten in the endosperm and the starch cells are firmly cemented together. In soft, low-protein wheat the bonding is not so firm. For most cakes a soft, low-protein flour is needed for. Flours used for pan bread production will generally be milled from hard wheat of high protein content, although soft wheat can give optimum quality in the type of bread that is most popular in some countries. Ideally, the flour will be non-chlorinated.

The choice of additional bakery ingredients will depend, of course, on the bakery product being produced. Indeed, the polydextrose according to the present invention can be used in the manufacture of bakery products such as cakes, biscuits, cookies, waffles, donuts, muffins, bread, fat-filling and bakery cream.

Dairy products of the invention can be selected from the group consisting of milk, whey, yoghurts and drinks based on them; dairy cocoa based drinks, fermented desserts (such as fresh cheese preparations, drinkable products), ice cream, neutral dairy desserts (such as puddings, flans, vlas, crème desserts, whipped desserts) and flavoured yoghurt preparations (e.g. fruit yoghurt without fruit). Ice cream prepared with the new polydextrose of the current invention, has a more full texture, is less watery, and shows a more fat-like creaminess and is very much appreciated for its rich taste and texture. The texture is better than the texture of ice cream using commercial polydextrose.

Beverage can be any medical or non-medical syrup or any drinkable solution including iced tea, and fruit juices, vegetable based juices, lemonades, cordials, and nut based drinks. It further encompasses beverage concentrates and drink powders. Beverage concentrate refers to a concentrate that is either in liquid form or in essentially dry mixture form. The liquid concentrate can be in form of a relatively thick, syrupy liquid. The essentially dry mixture can be in the form of either a powder or a tablet. The beverage concentrate is usually formulated to provide a drinkable beverage composition or a final beverage when constituted or diluted with water, either carbonated or non-carbonated. Drink powders are suitable for constituting with water, carbonated or non-carbonated, or milk, a final beverage for oral administration.

Said beverage can further comprising additional carbohydrates, proteins, peptides, amino acids, antioxidants, fats, vitamins, trace elements, electrolytes, intense sweeteners, edible acids, flavours and/or mixtures thereof.

Said additional carbohydrates are selected from the group consisting of monosaccharides, disaccharides, gelling starches, starch hydrolysates, dextrins, fibers such as low-caloric fibers, polyols and mixtures thereof.

The monosaccharides to be used as additional carbohydrates include tetroses, pentoses, hexoses and ketohexoses.

Typical disaccharides to be used as additional carbohydrates include sucrose, maltose, trehalulose, melibiose, kojibiose, sophorose, laminaribiose, isomaltose, gentiobiose, cellobiose, mannobiose, lactose, leucrose, maltulose, turanose and the like.

Starch hydrolysates to be used as additional carbohydrates are produced by the controlled acid or enzymatic hydrolysis of starch. They can be subdivided into two specific categories, maltodextrins and glucose syrups, and are characterized by their DE number (dextrose equivalent). In fact, the DE number is a measurement of the percentage of reducing sugars present in the hydrolysate and calculated as dextrose on a dry weight basis. Maltodextrins have a DE number up to 20, whereas glucose syrups have a DE number greater than 20.

Dextrins to be used as additional carbohydrates are prepared according to the dextrinisation method. Dextrinisation is a heat treatment of dry starch in presence or absence of acid.

Gelling starches to be used as additional carbohydrates may include emulsified starches such as starch n-octenyl succinate.

The low-caloric fibers can be arabinogalactan, chitosan, chitin, xanthan, pectin, cellulosics, konjac, gum Arabic, soy fiber, inulin, modified starch, hydrolysed guar, guar gum, beta-glucan, carageenan, locust bean gum, alginate, polyglycol alginate.

Among the vitamins one can mention vitamin A, vitamin C, vitamin D, vitamin E, vitamin $B_{12}$, and the like.

The edible acids can be selected from phosphoric acid, citric acid, malic acid, succinic acid, adipic acid, gluconic acid, tartaric acid, fumaric acid and mixtures thereof. Preferably the pH range of the beverage is from about 2 to about 6.5. These acids can be the same or different from the ones used in the crude polydextrose provision step.

The flavours are selected from fruit flavours, botanical flavour and mixtures thereof. Preferred flavours are cola flavour, grape flavour, cherry flavour, apple flavour and citrus flavours such as orange flavour, lemon flavour, lime flavour, fruit punch and mixtures thereof. The amount of flavour depends upon the flavour or flavours selected, the flavour impression desired and the form of flavour used.

If desired, coloring agents can also be added. Any water-soluble coloring agent approved for food use can be utilized for the current invention.

When desired, preservatives such as potassium sorbate and sodium benzoate can be added.

Gums, emulsifiers and oils can also be added in the beverage for texture and opacity purposes. Typical ingredients include carboxymethylcellulose, mono- and/or di-glycerides, lecithin, pulp, cotton seed oil and vegetable oil. It further can comprise foam stabilizing agents such as yucca, or yucca/quillaia extracts.

The invention will hereunder be illustrated in the form of a series of non-limiting examples.

EXAMPLES

Example 1

A separation test was performed with a chromatographical system (ISMB unit from Mitsubishi) composed of four chromatographic columns connected in series that had a bed volume (BV) of 300 liters. The column were packed with a strongly acidic cation (SAC) exchange resin (Mitsubishi UBK550 in $Na^+$-form), which was conditioned by passing deionized water through the column at 60° C. for 15 hours. The resin used was a copolymer made from styrene and divinylbenzene (DVB) with a cross-linking of 8%. The crude polydextrose (1.71 kg dry substance, composition: 1.5% contaminants including acid, 5.3% DP1, 8.4% DP2, 9.3% DP3, 9.0% DP4, 8.3% DP5, 7.5% DP5-DP10, 18.3% DP10-DP20, 22.4% DP20-DP30, 9.7% DP30-DP36 and 0.5% DP36+ by weight) was neutralised with an aqueous solution (30%) of sodium hydroxide to a pH close to 7.

The heated (55° C.) neutralised polydextrose solution (33.5° Brix) was then injected at the top of the column. The sample was then eluted with deionized water at a predetermined flow rate of 0.15 BV/hr and at a constant temperature of 50° C. Samples were collected at regular intervals, and 2 fractions have been isolated: one fraction containing the low molecular weight fraction and a second fraction containing the polydextrose (0.8 kg) with the desired molecular weight profile (see table 1-refined).

Results of the GPC analysis of the polydextrose (0.8 kg) with the desired molecular weight profile is shown in Table 1.

The GPC analysis was performed with two columns in series: Ultrahydrogel™ 500 (Waters Corp., USA) at ambient temperature and Rezex RSO Oligosaccharide (Phenomenex, USA) at 80° C.

The eluent is demineralised, degassed, sterile filtrated water, applied at a flow Rate of 0.2 ml/min Detector: Differential Refractometer and molecular Weight Calibration is done with Pullulan Standard Kit P-82 (Shodex, Japan) for MW 780.000-5.900, Cargill Polyol (e.g. Maltidex 163A6) for MW 828-180, and quantification is Electronical Integration.

TABLE 1

GPC analysis showing the composition of the combined fractions before and after applying the chromatographic step.

| Polymerisation degree | % DP + fractions | Molecular Weight | Crude | Refined |
|---|---|---|---|---|
|  |  | 22800-11800 | 0.0 | 0.04 |
|  |  | 11800-5900 | 0.5 | 2.1 |
| DP36-DP30 |  | 5900-4878 | 9.7 | 17.5 |
| DP30-DP20 |  | 4878-3258 | 22.4 | 33.5 |
| DP20-DP10 | DP20+: 74.74 | 3258-1638 | 18.3 | 21.6 |
| DP10-DP5 | DP10+: 82.24 | 1638-828 | 7.5 | 7.5 |
| DP5 | DP5+: 90.74 | 828 | 8.3 | 8.5 |
| DP4 |  | 666 | 9.0 | 6.7 |
| DP3 |  | 504 | 9.3 | 2.3 |
| DP2 |  | 342 | 8.4 | 0.2 |
| DP1 |  | 180 | 5.3 | 0.1 |
| Contaminants + acid |  | 180 * | 1.5 | 0.0 |

* contaminants + residual acid
* DP: degree of polymerization expressed in anhydroglucose units.

The neutralisation of the citric acid present in the unrefined polydextrose prior to the chromatographic separation step resulted not only in the removal of by-products like 5HMF, furfural, etc. but also prevented their formation.

Example 1B

Determination of Non-Digestible Fiber Content

The fiber content of the 'refined' polydextrose was measured by an in-vitro digestion system using rat intestinal enzymes. As a reference, isomaltulose was included.

The intestinal enzymes were purchased as rat intestinal acetone powder from Sigma. (Sigma catalogue #11630, Sigma-Aldrich, St. Louis, Mo., USA). The crude powder was further purified as described below:

10 g rat small intestinal acetone powder was added to 200 ml phosphate buffer pH 6.0, 0.1M and was mixed for 3 h at 4° C. The mixture was centrifuged at 10000 rpm for 10 minutes at 4° C. (Sorval RC5CPLUS—Kendro Laboratory Products, Newtown, Conn., USA). The supernatant was filtered on filter paper with vacuum followed by dialysis with membrane MWCO: 25000 (Spectra/Por Biotech Cellulose Ester (CE) Dialysis Membranes, Spectrum Laboratories, CA, USA) in buffer pH 6.0, 0.1M, 0.01% NaN3 (10 L and replace with fresh buffer every day) for 3 days at 4° C. while stirring gently with magnetic stirring bar. The obtained solution was lyophilized.

An activity check was done on the purified small intestinal rat powder. This was done with 0.06 g purified rat powder that was incubated with 5.4 ml 0.1 M phosphate buffer and addition of 0.6 ml 0.1% isomaltulose (final 0.01% isomaltulose). This was performed in a glass test tube at 37° C. and stirred with a small magnetic stirrer bar. Dextrose release was measured with a Glucose-Test kit (Reflectoquant 1.16720—Merck KgaA, Darmstadt, Germany. Purified rat powder that gave a minimum of 40 ppm dextrose after 60 minutes was used for fiber determination.

The polydextrose was incubated with intestinal enzymes under the following conditions 0.15 g purified rat intestinal powder was dissolved in 5.4 ml phosphate buffer pH 6.0, 0.05M. Subsequently, 0.6 ml sample at 0.1% was added. The reaction mixture was stirred gently and incubated at 37° C.

1 ml samples were taken after several time intervals and the amount of glucose present in each sample was determined immediately by Glucose-Test (Reflectoquant 1.16720—Merck KgaA, Darmstadt, Germany).

93% of non-digestible fiber was measured for the polydextrose sample whereas isomaltulose was fully hydrolysed after 2.3 hrs.

Example 2

Chocolate

The polydextrose of Example 1 was used to prepare dark chocolate and milk chocolate according to Tables 2 and 3, respectively.

TABLE 2

Dark chocolate composition

|  | % |
|---|---|
| maltitol | 10.00 |
| polydextrose | 19.00 |
| erythritol | 21.00 |
| cocoa mass | 45.44 |
| cocoa butter | 4.00 |
| sucralose | 0.013 |
| vanilla | 0.100 |
| lecithine | 0.450 |
| total | 100.00 |

The ingredients were mixed in a Z blender at 45° C. at a rate of 35 rpm for mixing and 50-60 for conching.

For producing dark chocolate, first, the sweetener (=maltitol, polydextrose, erythritol and sucralose) was put in the Z blender. Subsequently, part of the cocoa mass and the part of the cocoa butter was added. Refining was done with 3 rolls refiner. The powder obtained after the refining was put again into the Z blender for 1-3 h. The temperature of the Z blender was increased to 70° C. and the second part of the cocoa mass was added. After 14 h the second part of the cocoa butter was added. The temperature of the mixture was decreased to 50° C. One hour before the end of the process lecithin was added.

The chocolate is low caloric.

TABLE 3

Milk chocolate compositions

|  | 3-Way blend |
|---|---|
| maltitol | 10.00 |
| polydextrose | 18.50 |
| erythritol | 14.39 |
| cocoa mass | 13.50 |
| cocoa butter | 16.00 |
| Milk fat | 5.00 |
| Skimmed milk powder | 22.00 |
| sucralose | 0.020 |
| vanilla | 0.020 |
| lecithine | 0.570 |
| total | 100.00 |
| fat content | 29.1 |
| caloric value | 397.5 |

Table 3 shows a milk chocolate product comprising erythritol, maltitol and the polydextrose according to the invention (the 3-way blend)

The milk chocolate is low caloric. The final chocolate is non-cariogenic and the cooling effect of erythritol is reduced by the new polydextrose of the current invention.

Example 3

Ice Cream

In Table 4, three ice cream compositions comprising the polydextrose of example 1 are given.

Creamy ice cream can be prepared by applying the polydextrose according to example 1.

TABLE 4

| Ingredients | Fat-free | Sugar-free | Sugar-free |
|---|---|---|---|
| Maltitol syrup (Cargill C Maltidex M 16311) | — | 9.9% | 9.9% |
| Polydextrose (example 1) | 4.5% | 10.0% | 10.0% |
| Isomaltulose (Cargill Xtend 16420) | 10.0% | — | — |
| Whey powder (WPC 30) | 3.0% | 3.0% | 3.0% |
| Skimmed milk powder | 2.0% | 2.0% | 2.0% |
| Cocoa fat | — | 3.0% | — |
| Potato starch (Cargill, C DryLight 01970) | 2.5% | — | — |
| Fructose | 3.0% | — | — |
| Sucralose | — | 0.01% | 0.01% |
| Stabilizer (Danisco, Creamline 816) | 0.65% | 0.65% | 0.65% |
| Flavors | n.d. | n.d. | n.d. |
| Skimmed milk (<0,3% fat) | add to 100% | add to 100% | add to 100% |

The dry ingredients (apart from the fat) were mixed together. Everything was brought to a temperature of 40-45° C., followed by mixing in the water.

The fat was added and heating was started to pasteurize at 85° C. for 5 minutes, followed by homogenization at 80-85° C. in a two-step homogenizer at 150/50 bar. Product was brought through an in-line tubular heat exchanger (water cooled) to 25-30° C. and it was collected in a tank. Rapid cooling to 4° C. while stirring was continued and it was kept at 4° C. for a minimum of 4 hours (maturation).

The ice cream was extruded in a continuous freezer, outlet temperature −6 to −6.5° C. 1 L boxes were filled and put in a freezer at −35° C. for 16 hours and storage was done at −18° C.

The ice cream had a pleasant fat-like creaminess and was not watery, in comparison to the ice cream containing commercial polydextrose.

Example 4

Beverages

Carbonated Cola Beverages
Mid-calorie cola with 4% fructose, 3% polydextrose of Example 1 and high intense-sweetener

TABLE 5

| Recipe | | |
|---|---|---|
| Polydextrose | 188.1 | g |
| Aspartame | 466.2 | mg |
| Acesulfame K | 239.4 | mg |
| Caffeine anhydrous (ZX0116) | 0.57 | g |
| Fructose | 240 | g |
| Sodium benzoate 10% (w/v) | 9.5 | g |
| Cola emulsion AK 0610 (Duckworth) | 12.5 | g |
| Ortho-phosphoric acid 85% | 6.8 | g |
| add Spa ™ water to make | 1 | ltr |

Procedure:
The amount of Spa™ water was put in a beaker, the necessary amount of polydextrose was added and stirred until dissolution. The total mixture was heated up to max 50° C. Afterwards, the other ingredients were added until dissolution and heated up to max. 50° C.

Afterwards, 35 ml of this basic syrup was put into bottles and diluted with carbonated water to give a volume of 210 ml.

Evaluation:
The samples containing the polydextrose according to the invention got a specific density of approx. 7° Brix and a pH of approx. 2.7.

When compared to mixtures containing equivalent amounts of conventional polydextrose (Litesse®) instead, both had a good cola odor, but the one containing polydextrose according to the invention was less intense than conventional Litesse® polydextrose containing cola.

Color is not an issue within the cola formulations.
Taste:
The cola products containing the polydextrose according to the invention had a better cola taste than other conventional polydextrose cola drinks. The inventive products were judged to have a less artificial taste and no powdery taste.

Fruit Juice Containing Beverages
Low-calorie orange soft drink with 7% polydextrose of Example 1 and high intense sweetener

TABLE 6

| Recipe | | |
|---|---|---|
| Polydextrose | 72.68 | g |
| Aspartame | 225.5 | mg |
| Acesulfame-K | 112.24 | mg |
| Orange Compound JBA O11105-11 | 18 | g |
| Sodium benzoate 10% (w/v) | 1.5 | g |
| Citric acid monohydrate 50% (w/v) | 4.3 | g |
| Ascorbic acid 10% (w/v) | 0.8 | g |
| Add Spa ™ water to make | 1 | ltr |

Procedure:
The amount of Spa™ water was put in a beaker, the necessary amount of polydextrose was added and stirred until dissolution. The total mixture was heated up to max 50° C. Afterwards, the other ingredients were added until dissolution and heated up to max. 50° C.

Odor:
All samples had a good orange odor—no real difference

Taste:
Good orange perception, somewhat artificial aftertaste
Mid Calorie orange soft drink with 4% polydextrose of Example 1, 3% erythritol, and high intense-sweetener

TABLE 7

| Recipe | | |
|---|---|---|
| Polydextrose | 41.5 | g |
| Erythritol | 30 | g |
| Aspartame | 157.5 | mg |
| Acesulfame-K | 77.5 | mg |
| Orange Compound JBA 011105-11 | 18 | g |
| Sodium benzoate 10% (w/v) | 1.5 | g |
| Citric acid monohydrate 50% (w/v) | 4.3 | g |
| Ascorbic acid 10% (w/v) | 0.8 | g |
| Add Spa ™ water to make | 1 | ltr |

All samples had a dry matter of approx. 7.6° Brix and a pH of approx. 3.1.

Procedure:
The amount of Spa™ water was put in a beaker, the necessary amount of polydextrose was added and stirred until dissolution. The total mixture was heated up to max 50° C. Afterwards, the other ingredients were added until dissolution and heated up to max. 50° C.

Taste:
Good orange perception, nearly no artificial aftertaste

Example 5

Soft Gums

Soft gum recipes comprising no polydextrose (reference material), and polydextrose according to example 1

TABLE 8

| RECIPE | | | | |
|---|---|---|---|---|
| | | | Reference | Polydextrose |
| RAW MATERIALS | | | | |
| | Part A | Maltitol Cargill C*16313 | 3.5 | — |
| | | Polydextrose | — | 5 |
| | | Water | — | 2.14 |
| | | d.s. | 2.89 | 4.8 |
| | Part B | Gelatine 220 bl | 0.295 | 0.295 |
| | | Water | 0.421 | 0.421 |
| PROCESS | | | | |
| | Part A | Brix (after heating) | 86° | 83° |
| | Part B | Brix | 37.01 | 37.01 |
| | | d.s. | 0.265 | 0.265 |

Part A was dissolved in hot water (temperature 80-90° C.). It was kept at this temperature until the desired Brix was obtained.

Part B was dissolved in hot water of temperature of 90° C.

Part A and B (ratio A:B: 83/17) were mixed and citric acid was added to the blend. Depositing was occurring at temperature 78-84° C.

This method gave satisfactory results for the soft gums prepared with polydextrose of example 1

Example 6

In-Vitro Assessment of the Cariogenicity of Polydextrose of Example 1

Experimental

The method used was an in-vitro cariogenicity test. In this test 'in-vitro' fermentability of carbohydrates by the oral cavity bacterium *Streptococcus mutans*, was investigated under defined conditions. The test was set up as follows: In a medium, consisting of a simple nitrogen source with the test substance as sole carbon source, buffered with a physiological buffer, organic acid production was recorded over time.

a. Medium Constituents

Carbohydrate: 0.85M stock solution. Final concentration in test volume was 170 mM.

Nitrogen source: 6.7% d.s. Yeast Nitrogen Base (YNB from Difco). Final concentration in test was 0.67% d.s.

Buffer: 1.25M MES (morpholino-ethane-sulfonic acid) suspension was adjusted to pH=7.2 with concentrated NH4OH (MES is solubilised during pH adjustment). Final concentration in test was 0.25M.

The solutions were sterilized by filtration (0.22µ).

Each sterile 'in vitro' test tube (15×150 mm, metal stopper) contained the following ingredients (for a 10 ml test):

2 ml carbohydrate stock solution (0.85M)
2 ml MES-buffer
1 ml YNB-solution
4.5 ml sterile distilled water
0.5 ml inoculum A 5 ml test was generally used when low cariogenic substrates were tested, because of the high inoculum density, which was needed for these substrates; for cariogenic substrates (as sucrose, dextrose) the test was performed in 10 ml.

b. Inoculum Preparation

A stock culture was prepared by transferring *Streptococcus mutans*—TCV264 (ATCC25175) from TBAbase (Tryptose Blood Agar base) slants to TSB (Tryptic Soy Broth)—MES buffer (3% TSB-0.06M) in 1 L flask, pH7.2, and grown at 37° C. For 16 hours, 100 strokes/min shaking. Bacteria were concentrated by centrifugation (10 minutes at 3000 g). Cells were washed with physiological buffer (0.04% NaCl, 0.3 KH2PO4, 0.7% Na2HP04.2H2O, +0.5% Tween 80) and centrifuged again.

The final precipitate was re-suspended in a minimal volume (25 ml) of the same buffer, to contain approx. 2-5×10e10 cells/ml.

This stock culture was transferred into sterile REVCO-vials (1 ml/vial), immediately frozen in liquid nitrogen and stored at −70° C.

A vial with frozen *S. Mutans* cells was used to inoculate a sterile 0.5 L flask with 500 ml TSB-MES buffer, slightly agitating in a water-bath to disperse the cells. The culture was grown under the same conditions, as described above, during 5-7 hours (pH=6.3-6.4 and O.D. 660=0.8-0.9).

Cells were then harvested and re-suspended in 10 ml physiological buffer (=50× concentrated). Control platings on slants with Bile Esculin Agar were performed to check the purity and concentration of this cell-suspension.

Because of practical reasons and of the difficulty of viable cell count with Streptococci, the cell density was estimated several times by incubation of the inoculum on dextrose as substrate, with three different amounts of cells, and the acid production rate was observed. As inoculum for the test 1.0 ml of the above obtained suspension was used to inoculate the test tubes of the in vitro test.

All manipulations are carried out in a sterile environment.

c. In-Vitro Test Conditions and Sampling

Inoculated test tubes were incubated, without shaking, at 37° C. Test tubes were agitated on a Vortex, just before sampling. At appropriate time intervals, sterile samples (1.2 ml) were taken, centrifuged for 5' at 3000 g and supernatant was filtered through 0.45µ filter (non-sterile). The pH was measured. 0.75 ml samples were transferred.

Depending on the type of carbohydrate under investigation, different inoculum concentrations and different time intervals for sampling were chosen.

For polyols and alternative sweeteners, acid evolution was followed in a 16 to 40 hour interval, using approx. 5×10e9 cells/ml inoculum in the test tube.

For glucose, fructose, sucrose and other fermentable carbohydrates, the faster acid production requires an interval from 1 to 24 hours and a 10 times lower inoculum in the test tube.

Analysis and Calculation of Results

Organic acids were determined by HPLC on a Sodex KC811-column in H+form, at 65° C. And eluted with 0.01% H2SO4 at 0.8 ml/min and an injection volume of 25µ; detection with UV at 210 nm.

Areas of lactic, formic and acetic acid peaks were recorded and corrected with butyric acid as internal standard. HPLC results were expressed in micromol acid/ml or in mM.

The inoculum concentration used is 3.5×108 cells/ml. The release of organic acids was measured and ADR (total acidity/hr after a certain incubation period, mM/hr, total acidity is defined as the sum of lactic, formic and acetic acid).

The results are given in the next table:

TABLE 9

| Sample | ADR after 3 h | ADR after 5 h | ADR after 28 h |
|---|---|---|---|
| Polydextrose of example 1 | 3 | 3 | 1 |
| Mannitol | 0 | 0 | 0 |
| Isomaltulose | 4 | 5 | 5 |
| Commercial polydextrose | 6 | 5 | 2 |
| Litesse Ultra (commercial hydrogenated polydextrose) | 4 | 4 | 2 |

The in-vitro cariogenicity data indicate that the polydextrose of example 1 is essentially non-cariogenic and is even less cariogenic than the commercial polydextrose.

The invention claimed is:

1. A polydextrose fraction comprising saccharide molecules, the polydextrose fraction being a fraction separated from a crude polydextrose product by chromatographic separation,
    wherein the crude polydextrose product has been prepared by polymerization of saccharides in the presence of acid, wherein the acid is selected from the group consisting of phosphoric acid, citric acid, malic acid, succinic acid, adipic acid, gluconic acid, tartaric acid, fumaric acid and mixtures thereof, and the pH of the thus prepared crude polydextrose has been adjusted to from 6 to 8 prior to chromatographic separation;

wherein at least 90% by weight of the saccharide molecules in the polydextrose fraction have a degree of polymerisation of 5 or more, wherein at least 70% by weight of saccharide molecules have a degree of polymerisation of 10 or more, and wherein the non-digestible fiber content of the polydextrose fraction is at least 80% by weight.

2. The polydextrose fraction according to claim 1, wherein the molecular weight dispersity of the polydextrose fraction is below 2.0.

3. The polydextrose fraction according to claim 1, wherein the molecular weight dispersity of the polydextrose fraction is below 1.8.

4. The polydextrose fraction according to claim 1, wherein the polydextrose has a volume mean diameter that is smaller than 60 μm.

5. The polydextrose fraction according to claim 1, wherein the non-digestible fiber content of the polydextrose fraction is at least 85% by weight.

6. The polydextrose fraction according to claim 1, wherein the non-digestible fiber content of the polydextrose fraction is at least 90% by weight.

7. The polydextrose fraction according to claim 1, wherein less than 0.3% by weight of the saccharide molecules have a degree of polymerisation of from 1 to 2.

8. A process for preparing a polydextrose fraction comprising the following steps:
 a) providing a crude polydextrose prepared by polymerization of saccharides in the presence of acid, wherein the acid is selected from the group consisting of phosphoric acid, citric acid, malic acid, succinic acid, adipic acid, gluconic acid, tartaric acid, fumaric acid and mixtures thereof,
 b) adjusting the pH of the crude polydextrose to from 6 to 8 to yield a product comprising saccharide molecules, and
 c) chromatographic separation of the product of step b) into at a first polydextrose fraction and a second polydextrose fraction;
  wherein the first polydextrose fraction is enriched in saccharide molecules having a degree of polymerisation of from 1 to 4 compared to the product of step b); and
  wherein in the second polydextrose fraction:
   at least 90% by weight of the saccharide molecules in the polydextrose fraction have a degree of polymerisation of 5 or more,
   wherein at least 70% by weight of saccharide molecules have a degree of polymerisation of 10 or more, and
   wherein the non-digestible fiber content of the polydextrose fraction is at least 80% by weight; and
 d) collecting the second polydextrose fraction.

9. The process according to claim 8, wherein the crude polydextrose is provided by polycondensation of saccharides, and optionally sugar alcohols in the presence of acid.

10. The process according to claim 8, wherein the chromatographic separation of step c) comprises chromatographic separation on a strongly acidic cation exchange resin.

11. The process according to claim 8, wherein the pH of the crude polydextrose is adjusted to about 7.

12. The process according to claim 8, wherein in the second polydextrose fraction, the molecular weight dispersity of the polydextrose fraction is below 2.0.

13. The process according to claim 8, wherein in the second polydextrose fraction, less than 0.3% by weight of the saccharide molecules have a degree of polymerisation of from 1 to 2.

14. The process according to claim 8, wherein the crude polydextrose product has been prepared by polymerization of saccharides in the presence of acid, wherein the acid is selected from the group consisting of citric acid, malic acid, succinic acid, adipic acid, gluconic acid, tartaric acid, fumaric acid and mixtures thereof.

* * * * *